United States Patent [19]

Arora

[11] Patent Number: 5,223,257

[45] Date of Patent: Jun. 29, 1993

[54] TOPICAL COMPOSITION FOR RELIEVING ACHES AND PAINS

[76] Inventor: Vasu Arora, P.O. Box 2685, Grundy, Va. 24614

[21] Appl. No.: 850,958

[22] Filed: Mar. 11, 1992

[51] Int. Cl.5 .................. A61K 35/78; A61K 31/60
[52] U.S. Cl. .................. 424/195.1; 514/159; 514/825; 514/887; 514/783
[58] Field of Search .......... 424/401, 195.1, 78.05; 514/825, 817, 783, 887

[56] References Cited

U.S. PATENT DOCUMENTS

| | | | |
|---|---|---|---|
| 2,113,374 | 4/1938 | Hall | 260/111 |
| 2,257,166 | 9/1941 | Christiansen | 167/58 |
| 3,184,388 | 5/1965 | Kalopissis | 167/90 |
| 3,880,996 | 4/1975 | Fisher | 424/184 |
| 4,120,976 | 10/1978 | Hosick | 514/825 |
| 4,353,896 | 10/1982 | Levy | 514/936 |
| 4,742,083 | 5/1988 | Ritchey | 514/618 |
| 5,013,726 | 5/1991 | Ivy | 514/159 |

*Primary Examiner*—Thurman K. Page
*Assistant Examiner*—Sally Gardner
*Attorney, Agent, or Firm*—Jacobson, Price, Holman & Stern

[57] ABSTRACT

A composition comprising approximately equal proportions by volume of wintergreen oil, olive oil and/or oil of Eucalyptus and alcohol has an analgesic effect in treating aches and pains when rubbed or massaged on skin covering tissue from which such aches or pains emanate.

11 Claims, No Drawings

TOPICAL COMPOSITION FOR RELIEVING ACHES AND PAINS

FIELD OF THE INVENTION

Compositions comprising approximately equal parts by volume of methyl salicylate, olive oil and alcohol, when rubbed on or massaged into skin relieve muscle aches and pains in the proximate area. The olive oil is, optionally, partially or wholly replaced by oil of Eucalyptus

BACKGROUND

Methyl salicylate has been reported as useful in the preparation of therapeutic agents for both oral and topical administration. Hall (U.S. Pat. No. 2,113,374) indicates an analgesic effect from topical administration of a lotion or ointment (which optionally contains alcohol) comprising a reaction product of an alkyl salicylate with a polyhydric alcohol for treatment of such ailments as neuralgia, neuritis and rheumatism, as well as for sprains and bruises. Fisher (U.S. Pat. No. 3,880,996) provides an analgesic composition for local application for enhanced salicylate absorption and alleviation of musculo-skeletal pain; his composition includes a salicylate analgesic, a rubefacient, a minor amount of silicone and, optionally, a suitable carrier or vehicle.

SUMMARY OF THE INVENTION

Compositions containing substantially equal amounts by volume of methyl salicylate, olive oil and/or oil of Eucalyptus and alcohol, when massaged into or rubbed on skin, relieve pains and aches emanating from tissue below the skin so rubbed or massaged. The aches can be muscular aches; the pain may be caused by arthritis of joints. The compositions also have an anti-inflammatory effect.

An object of the invention is to provide a topically applicable composition for relieving aches and pains which emanate from areas close to the skin. A further object is to prepare the composition in lotion, cream, ointment or salve form. Another object is to relieve muscular aches or pains, back ache, joint pain, myositis, neuralgia and neuritis by massaging the proximate area while rubbing the composition thereon. Still further objects will be apparent from the following description.

DETAILS

The compositions have three essential constituents: methyl salicylate (wintergreen oil), olive oil and alcohol in approximately equal proportions. The amount of each can actually vary from about 25 to about 40 (preferably from about 30 to about 35) parts by volume per 100 parts by volume of all three. The olive oil is optionally at least partially replaced by oil of Eucalyptus.

Typical compositions in parts by volume are exemplified in the following table.

TABLE

| | COMPOSITIONS | | | |
|---|---|---|---|---|
| | Methyl Salicylate | Olive Oil | Oil of Eucalyptus | Isopropyl Alcohol |
| 1 | 30 | 20 | 20 | 30 |
| 2 | 35 | 35 | — | 30 |
| 3 | 35 | — | 35 | 30 |
| 4 | 30 | 20 | 15 | 35 |
| 5 | 35 | 10 | 25 | 30 |
| 6 | 40 | 30 | 5 | 25 |
| 7 | 35 | 5 | 30 | 30 |

Although the noted components may be the sole components of the composition, they are optionally combined with any suitable carrier so that the resulting composition is in the form of a lotion, cream, ointment or salve. In the latter event the carrier is a conventional carrier, the only requirements for which are that it be topically acceptable and compatible with the essential constituents; no component of the carrier can be chemically reactive with any of the three or four essential constituents. When a carrier is employed, it is advantageous for the resulting composition to be storage stable, but such is not required when such resulting composition is in lotion or cream form, since the latter can be shaken, if necessary, immediately prior to use.

The preferred olive oil is pure, virgin, naturally cold processed Italian olive oil, such as Bertolli TM olive oil, and the preferred alcohol is isopropyl alcohol. When the essential constituents are combined with a carrier, they constitute a proportion of the resulting composition which is effective to relieve aches and pains emanating from tissue in close proximity to the skin surface rubbed or massaged with such composition The compositions are applied for periods of from 5 to 10 minutes each three to four times each day, or as needed, until the involved aches or pains subside If the respective constituents separate while standing, the composition should be adequately shaken prior to use to make certain that the several essential ingredients are applied in appropriate proportions The invention and its advantages are readily understood from the foregoing description. Various changes may be made in the compositions and the method of use without departing from the spirit and scope of the invention or sacrificing its material advantages The compositions and methods of use hereinbefore described are merely illustrative of preferred embodiments of the invention.

What is claimed is:

1. A composition which consist essentially of a combination of the following: a) methyl salicylate, b) olive oil and/or oil of Eucalyptus and c) alcohol, each of (a), (b) and (c) being in an amount of from 25 to 40 parts by volume per 100 parts by volume of the sum of (a), (b) and (c).

2. A composition of claim 1 wherein the alcohol is isopropyl alcohol.

3. A composition of claim 2 wherein the olive oil is Italian olive oil.

4. A composition of claim 1 which consists essentially of methyl salicylate, olive oil, oil of Eucalyptus and alcohol.

5. A composition consisting essentially of a combination of the following constituents: a) methyl salicylate, b) olive oil and/or oil of Eucalyptus and c) alcohol, each of (a), (b) and (c) being in an amount of from 30 to about 35 parts by volume per 100 parts by volume of all three.

6. A composition of claim 5 which consists essentially of methyl salicylate, olive oil and alcohol.

7. A composition of claim 5 which consists essentially of methyl salicylate, oil of eucalyptus and alcohol.

8. A topically administrable composition of claim 1 in the form of a cream or lotion.

9. A topically administrable composition of claim 1 in the form of an ointment or salve 10. A method of relieving ache or pain which comprises topically rubbing or massaging skin in the proximate area of the ache or pain with an amount of a composition of claim 1 effective relieve ache or pain.

11. A method of claim 10 which comprises rubbing or massaging for periods of from 5 to 10 minutes 3 or 4 times a day.

* * * * *